(12) United States Patent
Zhang et al.

(10) Patent No.: US 7,367,955 B2
(45) Date of Patent: May 6, 2008

(54) COMBINED LASER SPIROMETER MOTION TRACKING SYSTEM FOR RADIOTHERAPY

(75) Inventors: Tiezhi Zhang, Madison, WI (US); Harald Keller, Madison, WI (US); Bhudatt R. Paliwal, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 608 days.

(21) Appl. No.: 10/715,986

(22) Filed: Nov. 18, 2003

(65) Prior Publication Data

US 2004/0254492 A1 Dec. 16, 2004

Related U.S. Application Data

(60) Provisional application No. 60/478,584, filed on Jun. 13, 2003.

(51) Int. Cl.
*A61B 5/08* (2006.01)
(52) U.S. Cl. .................. 600/534; 600/529; 600/538
(58) Field of Classification Search ............. 600/534, 600/538

See application file for complete search history.

(56) References Cited

U.S. PATENT DOCUMENTS

| | | | | |
|---|---|---|---|---|
| 4,373,534 A | * | 2/1983 | Watson | 600/538 |
| 4,815,473 A | * | 3/1989 | Watson et al. | 600/534 |
| 6,062,216 A | * | 5/2000 | Corn | 128/204.23 |
| 6,144,875 A | | 11/2000 | Schweikard et al. | |
| 6,385,286 B1 | | 5/2002 | Fitchard et al. | |
| 6,413,225 B1 | * | 7/2002 | Sackner et al. | 600/529 |
| 6,959,266 B1 | * | 10/2005 | Mostafavi | 702/189 |
| 2002/0115923 A1 | | 8/2002 | Erbel | |
| 2002/0120207 A1 | | 8/2002 | Hoffman | |
| 2004/0116804 A1 | * | 6/2004 | Mostafavi | 600/428 |

OTHER PUBLICATIONS

Robinson, T.E., et al.; "Standardized High-Resolution CT of the Lung Using A Spirometer-Triggered Electron Beam CT Scanner"; AJR:172; Jun. 1999; pp. 1636-1638.*

Aliverti, Andrea, et al., Optoelectronic Plethysmography in Intensive Care Patients, Am J Respir Crit Care Med, vol. 161, pp. 1546-1552, 2000, U.S.A.

* cited by examiner

*Primary Examiner*—Robert L. Nasser, Jr.
*Assistant Examiner*—Karen E Toth
(74) *Attorney, Agent, or Firm*—Boyle Fredrickson, S.C.

(57) ABSTRACT

An improved non-invasive respiration monitor combines signals from a spirometer and laser chest displacement sensor to reduce signal error. The improved respirations signal can be used for position correction in radiation therapy and imaging applications and can be displayed to a user in breath control techniques.

21 Claims, 6 Drawing Sheets

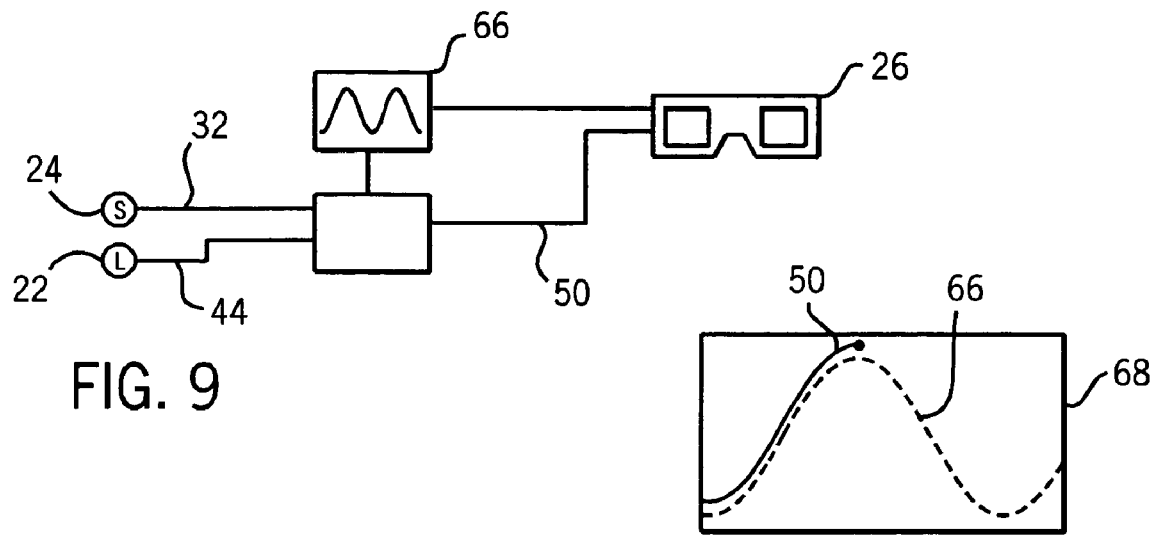
FIG. 9
FIG. 10
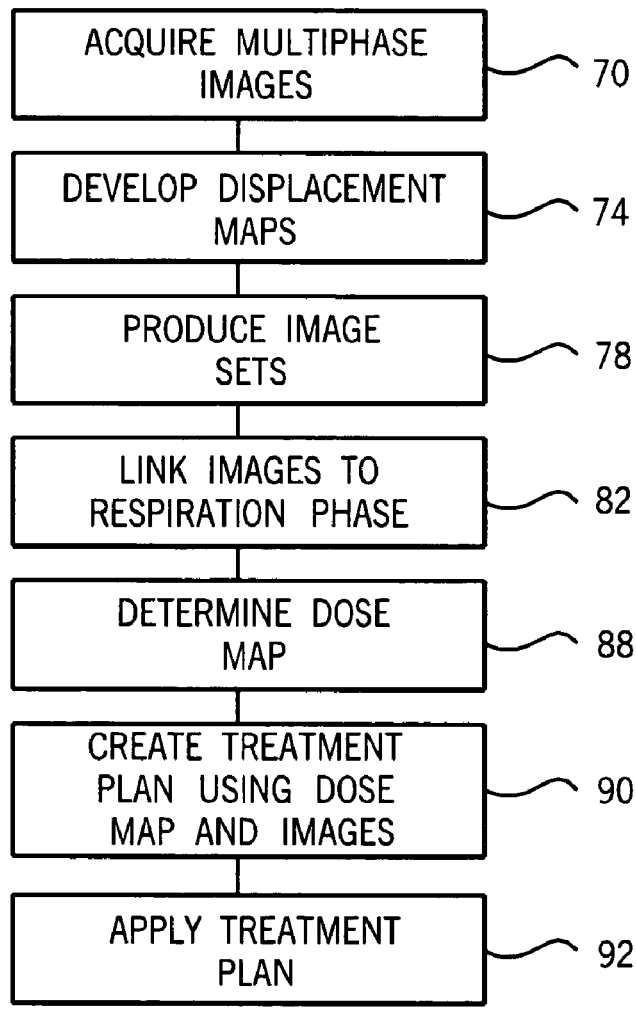
FIG. 11

COMBINED LASER SPIROMETER MOTION TRACKING SYSTEM FOR RADIOTHERAPY

CROSS-REFERENCE TO RELATED APPLICATIONS

This application claims the benefit of U.S. Provisional application 60/478,584 filed Jun. 13, 2003 which is hereby incorporated by reference.

STATEMENT REGARDING FEDERALLY SPONSORED RESEARCH OR DEVELOPMENT

This invention was made with United States government support awarded by the following agencies: NIH CA 88960. The United States has certain fights in this invention.

BACKGROUND OF THE INVENTION

The present invention relates to respiration sensing equipment and in particular to a respiration sensing device suitable for monitoring respiration during radiation therapy during breath-hold protocols and synchronized breathing protocols.

Accurate monitoring of a patient's breathing can be important in a wide variety of medical applications. In imaging, an accurate knowledge or respiration phase may be used to properly assemble x-ray tomographic or magnetic resonance imaging components acquired during breathing into an image free of image artifacts. In radiation therapy, accurate knowledge of respiration phase may be used to steer or limit the radiation beam to accurately apply radiation to the correct tissue. In a new radiation treatment delivery described in application U.S. Ser. No. 10/702,810 filed on Nov. 6, 2003 and hereby incorporated by reference, accurate knowledge of the respiration phase is used to synchronize the treatment plan phase and respiration phase allowing continuous breathing by the patient during treatment to produce an imaging and radiation treatment.

Current systems for monitoring respiratory motion include: (1) chest displacement sensors that track the surface of the abdomen by measuring the position of a reflective marker on the chest with a fixed camera or by measuring the distance from a fixed point to the surface of the abdomen using a laser-based distance sensor, (2) spirometers measuring air flow into and out of the patient's lungs, and (3) internal markers placed on tissue of interest and monitored using x-rays, magnetic fields, or the like.

Although invasive internal markers provide the most reliable method of target position tracking, convenient non-invasive chest displacement or flow measurement spirometers are widely used in a radiotherapy clinic. Yet, these latter systems have significant disadvantages. Chest displacement systems are strongly affected by variations in set-up. Radiation treatment can extend over many sessions so it is not easy to reproduce the same measurements over the entire course of treatment. Spirometer systems measure air flow only and this signal must be integrated to obtain air volume as a function of time such as provides a measure of respiration. Slight errors in flow measurement accumulate in time and cause signal drift. Generally, spirometers exhibit a nonlinear response to air flow.

When the respiration signal is used for determining precise positioning of tissue for imaging or radiation treatment, set-up sensitivity and drift are significant problems.

SUMMARY OF THE INVENTION

In the present invention, a spirometer is connected to the patient with a mouth piece and a laser displacement sensor is used to measure abdomen surface position. A computer collects the signals. Two working modes are possible. In spirometer mode, the spirometer signal drift is corrected periodically by the laser. In laser mode, the correlation of a spirometer signal and a laser signal is first obtained and then used to calibrate the laser displacement reading into volume reading.

Specifically, the present invention provides a respiration monitor having a spirometer adapted to receive air flow from a patient's lungs with breathing to provide an air flow signal and a chest displacement sensor adapted to monitor displacement of the patient's chest with breathing to provide a chest displacement signal. A calibration circuit receiving the air flow signal and the chest displacement signal provides a corrected respiration signal combining information from both the air flow signal and the chest displacement signal.

Thus it is one object of the invention to provide a high quality non-invasive respiration monitor that avoids the drawbacks to chest displacement sensors and spirometers alone.

The calibration circuit may include an integrator receiving the air flow signal to produce a lung volume signal; and a baseline corrector receiving the lung volume signal and the chest displacement signal to correct an integration offset of the lung volume signal to produce the corrected respiration signal based on the chest displacement signal.

Thus it is another object of the invention to correct for integrator drift in a spirometer such as prevents the respiration signal from accurately indicating tissue position over time.

The correction of integration offset may occur periodically at a predetermined phase of respiration by setting the lung volume signal equal to a stored calibration value.

Thus it is another object of the invention to provide regular corrections that avoid accumulation of significant error.

The calibration value is a previous value of the lung volume signal at the predetermined phase.

Thus it is another object of the invention to provide a simple source of a correction value.

In an alternative embodiment, the calibration circuit may include an integrator receiving the air flow signal to produce a lung volume signal; and a model of the relationship between lung volume and chest displacement signal, the model receiving the chest displacement signal to provide a lung volume signal as the corrected respiration signal.

Thus it is another object of the invention to provide a simple calibration of the chest displacement signal that corrects for set-up variations.

The model may be a linear function relating chest displacement signal to lung volume such as a multiplier multiplying the chest displacement signal by a factor determined from a correlation between the lung volume signal and the chest displacement signal to produce the corrected respiration signal. Alternatively, the model may be a non-linear function relating chest displacement signal to lung volume such as may be implemented in a lookup table recording a relationship between lung volume and chest displacement for at least one cycle of breathing, the lookup table receiving chest displacement signal to output the corrected respiration signal.

Thus it is another object of the invention to provide a range of correction techniques providing for flexible implementation of a correction to the chest displacement signal.

The model may provide a different functional relationship between chest displacement signal and lung volume during inspiration and exhalation.

Thus it is another object of the invention to correct for hysteresis present in the chest displacement signal.

The model detects a breath-hold from the chest displacement signal and hold the corrected respiration signal constant until an end of the breath-hold.

Thus, it is another object of the invention to provide a method for correcting chest displacement signal drift during breath-holds when a breath-hold treatment technique is used.

The invention may be used with a controllable radiation source receiving the corrected respiration signal to control radiation delivered to a patient according to the respiration signal. Alternatively, the invention may be used with an imager receiving the corrected respiration signal and acquiring component image signals from a patient over different phases of respiration, and mathematically combining the component image signals according to phases of respiration when the component image signals were acquired to produce a composite image.

It is therefore another object of the invention to enable improved radiation treatment or imaging of moving tissue by providing a respiration signal that provides improved indication of tissue position, not just respiration phase.

The respiration monitor may further includes a patient display displaying the corrected respiration signal to the patient.

Thus it is another object of the invention to provide a respiration signal that can be presented to a patient for control of his or her breathing.

These particular objects and advantages may apply to only some embodiments falling within the claims and thus do not define the scope of the invention.

BRIEF DESCRIPTION OF THE DRAWINGS

FIG. 9 is a block diagram of a visual feedback system that may be used in the system of FIG. 1 providing a corrected respiration signal and a breathing pattern signal to the patient;

FIG. 10 is a simplified representation of the display of the visual feedback system of FIG. 9;

FIG. 11 is a flow chart of the steps employed in the present invention to generate a treatment plan for the system of FIG. 1 that is corrected for lung motion;

DETAILED DESCRIPTION OF THE PREFERRED EMBODIMENT

System Architecture

Figure 1:
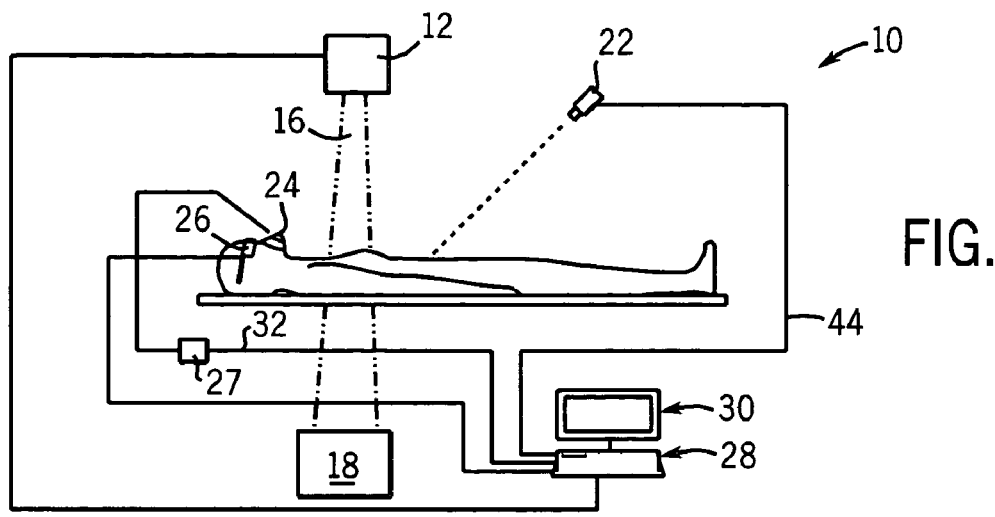
FIG. 1 is a block diagram of a laser-spirometer combined system showing a laser producing a chest displacement signal and spirometer producing a lung volume signal for respiration measurement and a patient positioned to radiation therapy treatment.

Referring now to FIG. 1, an intensity modulated radiation therapy (IMRT) system 10 suitable for use with the present invention provides a radiation source 12. As is understood in the art in a second generation IMRT, the radiation source 12 is a fan beam and may orbit around a patient 14 in a rotational plane parallel to the plane of the fan beam and perpendicular to the plane of the figure transmitting a multi-beamlet radiation beam 16 through the patient 14 to be received by a detector device 18 and/or a radiation stop. The radiation source 12 may be supported for such rotation on a gantry (not shown).

In a first generation IMRT system, the radiation source is a cone beam also positionable about the patient 14, typically to a few selected angles (6-10).

The fan or cone beams are intensity modulated to achieve the best dose distribution according to a physician's prescription.

The system shown is also representative of a tomographic imaging system in which case the radiation source 12 is not modulated and the detector device collects projection images to be mathematically combined in a tomographic image according to methods well known in the art.

The patient 14 may be supported in a supine position on a table 20 and the patient's respiration monitored using conventional respiration monitoring such as a chest cuff, displacement sensor, or spirometer.

Alternatively, and as will be described below, the patient's respiration may be monitored with an improved respiration monitor. In this case, the patient is positioned so that a laser displacement sensor 22 (or other displacement sensors) may monitor respiratory motion of the patient's chest. The patient 14 may further breathe through a spirometer 24 measuring airflow into and out of the patient's lungs and the patient may wear video glasses 26 to provide for feedback with respect to the patient's breathing as will be described.

The signal from the spirometer 24 may be preprocessed by an integrator 27 to provide a lung volume signal to a controlling computer 28 which may alternatively receive the signal from the spirometer 24 directly and implement the integrator 27 internally. The computer 28 may also receive a displacement signal from the laser displacement sensor 22 and may communicate with a control terminal 30 such as may include a video screen, keyboard, and mouse or the like. The computer 28 may further control delivery of radiation from the radiation source 12 about the patient 14 and the intensity of the beamlets of the beam 16 by shutters or moving leaves according to methods well known in the art. In the case of an imaging system, the computer may collect the projections and perform a tomographic reconstruction.

Development of an Accurate Respiration Signal

Figure 2:
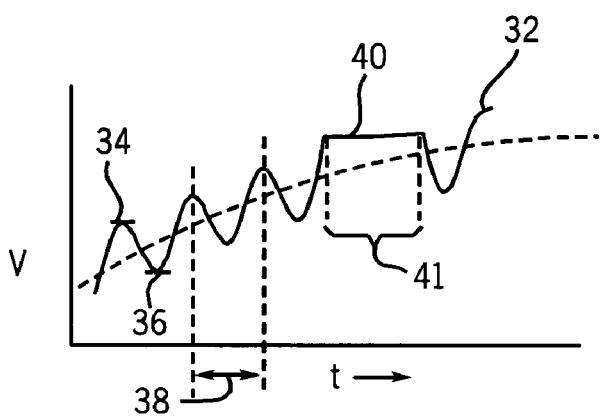
FIG. 2 is a graph of a typical spirometer lung volume signal during both regular breathing and a breath-hold showing drift in the signal.

Referring now to FIG. 2, a typical lung volume signal 32 derived from spirometer 24 shows peaks 34 and troughs 36 corresponding, respectively, to full inspiration and full expiration by the patient 14 during a regular breathing period 38. The present invention contemplates treatment of the patient 14 without the need for breath-holding, however, the respiration signal developed for the present invention may also find use with breath-hold protocols and therefore, the lung volume signal 32 during breath-hold is also shown. During the breath-hold, a plateau 40 is created in the lung volume signal 32 reflecting constant lung volume during this breath-hold period 41.

The integration of the output of the spirometer 24 to convert its flow signal (volume/time as a function of time) into a lung volume signal (volume as a function of time) may result in drift, as shown generally by the dotted trend line 42, caused by the integration over time of small offsets in the spirometer signal. Such baseline drift can be confusing to a patient 14 who is attempting to match his or her breathing, as indicated by this drifting signal, to a standard breathing guiding pattern which does not drift.

Figure 3:
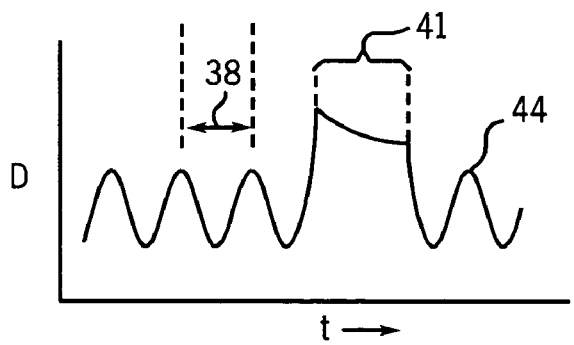
FIG. 3 is a graph of a typical laser chest displacement signal showing a chest contraction at the beginning of a breath-hold.

Referring now to FIG. 3, drift is largely absent from the laser chest displacement signal 44 which does not employ the integrator required of the spirometer 24 but measures chest displacement directly. Generally, the breathing period 38 of the laser chest displacement signal 44 will match the breathing period 38 of the spirometer lung volume signal 32, but the laser chest displacement signal 44 provides a displacement output rather than an output of lung volume. Signal amplitude range variations due to daily setup variations cause deviations between lung volume and chest displacement. Also, during the breath-hold period 41, the laser chest displacement signal 44 decays because of muscle relaxation despite the lack of change in lung volume.

Figure 4:
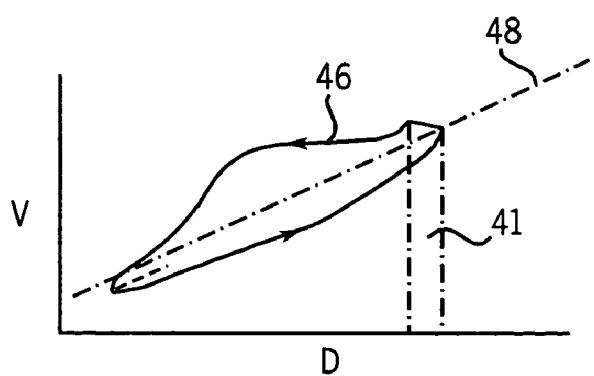
FIG. 4 is a graph of the lung volume signal versus the chest displacement signal showing their correlation and hysteresis.

Referring now to FIG. 4, during a single breathing period 38, there is strong correlation between the lung volume signal 32 obtained from the spirometer 24 and the chest displacement signal 44 from the laser displacement sensor 22 as illustrated by correlation curve 46. The correlation curve 46 plots the lung volume signal 32 on the vertical axis against chest displacement signal 44 on the horizontal axis for one breathing period 38. The points of the correlation curve 46 may be fit to a slope line 48 by a least square fit or other techniques wherein the slope of the slope line 48 provides the correlation between the lung volume signal 32 and the chest displacement signal 44. Generally, the correlation curve 46 will have some hysteresis meaning that the functional relationship between lung volume and chest displacement as displacement increases is different from the functional relationship between the lung volume and the chest displacement as displacement decreases. The correlation failure between lung volume signal 32 and the chest displacement signal 44 during a breath-hold of breath-hold period 41 is shown by a short flat area in the correlation curve 46.

Because of the drift noted in the lung volume trend line 42 noted above in FIG. 2, correlation curve 46 will generally rise or fall over time preserving approximately the same shape and slope line 48.

Figure 5:
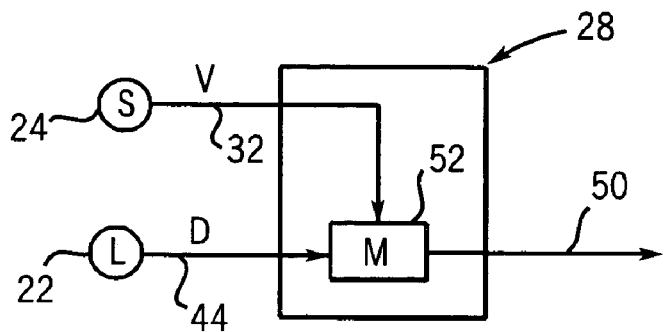
FIG. 5 is a block diagram of the processing of the lung volume signal and chest displacement signal of FIG. 1 to modify the chest displacement signal to produce a corrected respiration signal.

Referring now to FIG. 5, a corrected respiration signal 50 may be obtained by using both the lung volume signal 32 and the chest displacement signal 44 to provide a corrected respiration signal 50 that is both relatively free from drift, calibrated in units of volume, and free from breath-hold artifacts. This correction process may be implemented by model 52 realized preferably as a program running in computer 28.

In a first embodiment, the model 52 receives the lung volume signal 32 and the chest displacement signal 44 to deduce the slope of the slope line 48. The chest displacement signal 44 is then scaled by the slope to translate the chest displacement into units of lung volume but without drift as the corrected respiration signal 50.

Figure 6:
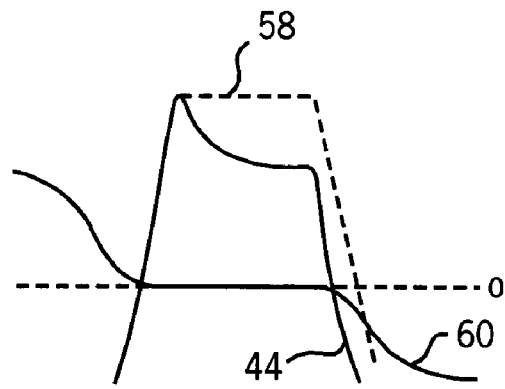
FIG. 6 shows a breath-hold detection system that may be used with the processing of FIG. 5 to further correct the chest displacement signal.

Referring now to FIG. 6, when breath-hold measurements are required, the model 52 may provide for breath-hold-detection to hold corrected respiration signal 50 constant when a breath-hold is detected. In one embodiment, the breath-hold detection may monitor the laser chest displacement signal 44. Breath-hold can be detected from the shape of the chest displacement signal 44 in which the derivative of this signal changes abruptly at the beginning and ending of breath-hold or from spirometer signal 60 in which the flow reading is zero during breath-hold. When a breath-hold is detected, the corrected respiration signal 50 is held to a constant value 58 until the breath-hold is over. Such a system may be used to eliminate the decay artifact of the laser chest displacement signal 44 during the breath-hold period 41.

In a second embodiment, the correlation curve 46 may be captured as a lookup table fitted to a nonlinear equation and used to map arguments of the chest displacement signal 44 to values of lung volume according to the function captured by the correlation curve 46. By detecting an instantaneous change in the input of the chest displacement signal 44 and using the direction of this change to apply the chest displacement signal to either the upper or lower portion of the correlation curve 46, respectively, a model 52 that accommodates hysteresis can be obtained. The use of correlation curve 46 to convert the chest displacement signal 44 into values of lung volume effectively eliminates the decay artifact in the chest displacement signal 44 because the flat portion of the correlation curve 46 during breath-hold period 41 holds lung volume output constant during the breath-hold period 41. The correlation curve 46 may be an average of a number of breathing periods 38 after baseline correction.

Figure 7:
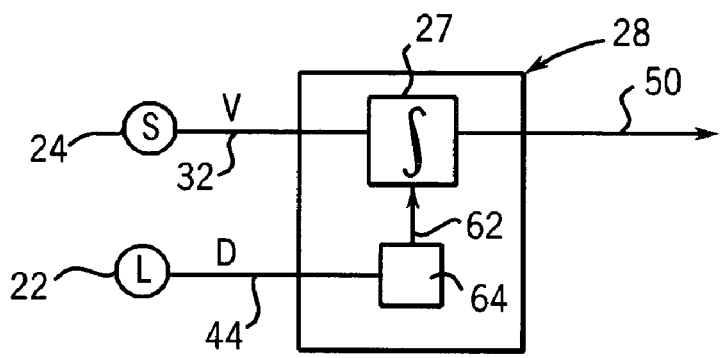
FIG. 7 is a block diagram similar to FIG. 5 of the processing of the lung volume signal and chest displacement signal of FIG. 1 to modify the lung volume signal to produce a corrected respiration signal.

Referring to FIG. 7, the lung volume signal 32 from the spirometer 24 and the chest displacement signal 44 from the laser displacement sensor 22 may also be used to correct the lung volume signal 32 to be the corrected respiration signal 50. In this case, the integrator 27 is preferably implemented within the computer 28 so that the integration constant can be controlled directly. Per this correction process, a correction value is provided by constant generator 64 at a regular period at a given phase in the respiration cycle as determined by the laser displacement sensor (as shown) or the spirometer 24. The correction value is preferably a stored sample of the lung volume signal 32 at the given phase from an early time in the monitoring of respiration when the spirometer signal baseline drift is negligible.

Figure 8:
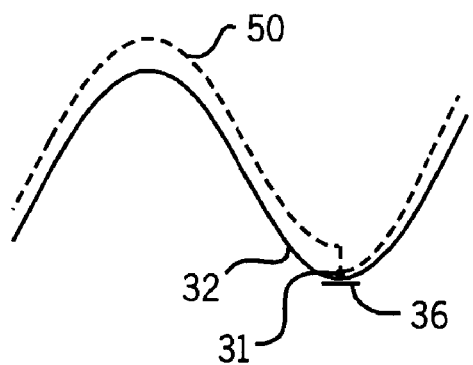
FIG. 8 is a plot of the lung volume signal of FIG. 7 as corrected to produce the corrected respiration signal.
Figure 12:
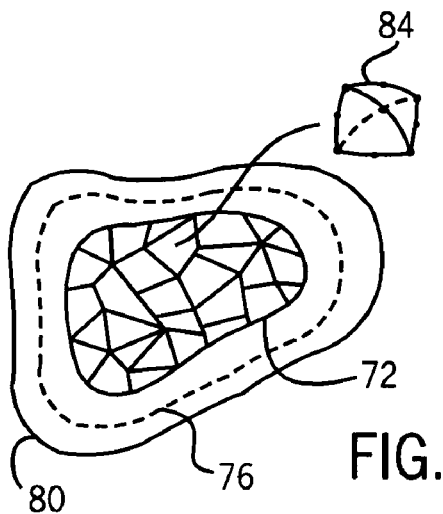
FIG. 12 is a cross-section through a lung of a patient during three stages of the breathing cycle showing generation of a solid model in the lung at a full expiration stage of breathing.

Thus, referring to FIG. 8, at the given phase of the breathing cycle, (for example, full expiration 36) the spirometer lung volume signal 32 is recorded as reference reading 31. The chest displacement signal 44 (not shown) may also be recorded to identify the given phase of the breathing cycle. For later operation, when chest displacement signal 44 reaches the same respiratory phase (amplitude) as the recorded point, the corrected respiration signal 50 is set back to the reference reading 31. In this way, spirometer signal drift is corrected for every cycle and is thereby very small.

Referring now to FIG. 9, the corrected respiration signal 50 may be displayed to the patient 14 via the glasses 26 together with a pre-established standard breathing guiding pattern 66 preferably obtained from measurements both of the amplitude and periodicity of the patient's ordinary respiration. In this case, the standard breathing guiding pattern 66 may be measured from the patient 14 using the techniques described above and the corrected respiration signals 50 during that measurement stored in computer memory.

Referring to FIG. 10, the display 68 of the glasses 26 may show to the patient a full cycle of the standard breathing guiding pattern 66 and a repeatedly drawn corrected respiration signal 50 updated in real time with the horizontal axis scrolling from left to right. The patient 14, observing the corrected respiration signal 50 for his or her current breathing, and the standard breathing guiding pattern 66, may be instructed to conform their breathing to the standard breathing guiding pattern 66. This ability to synchronize the patient's breathing with a stored pattern makes possible the preparation of a treatment plan that is keyed to the standard breathing guiding pattern 66 and which may thus compensate for movement of a tumor in the lung or closely adjacent thereto.

Whereas the present invention does not require breath-hold, the spirometer laser correction system of the present invention may also provide advantages when used in conventional breath-hold situations. Further, it will be understood that the chest displacement signal 44 need not be a laser sensor, but other chest displacement methods including other optical techniques, cuffs, and mechanical transducers may be used.

Use with an Imaging System

Many imaging modalities including x-ray tomography and magnetic resonance imaging create images using a set of measurements acquired over a considerable length of time during which regular physiological motion such as breathing may occur. These measurements which may be x-ray projections or resonance signals acquired with a given set of magnetic gradients are mathematically combined to produce an image. Changes in the position of the tissue during this acquisition process may cause artifacts in the reconstructed images. The present invention may be used to provide a robust respiration signal that may be used to time or order acquisitions according to known techniques to minimize or eliminate these artifacts.

Radiation Therapy with Synchronized Breathing

As will be described in more detail below in the present invention, a treatment plan can be developed for controlling the intensity of the various rays of the radiation source 12 to treat tumor tissue on or near the patient's lungs or other organ having predictable motion. The treatment plan will be provided by the computer 28 which will coordinate operation of the radiation source 12 according to a respiration signal so as to treat the patient 14 during movement of the tumor. During the treatment, the patient 14 may observe a predetermined breathing guiding pattern through the glasses 26 to synchronize his or her breathing to a breathing guiding pattern used in preparation of the treatment plan.

Referring now to FIG. 11, in the first step of preparing a treatment plan as indicated by process block 70, CT images are acquired at multiple phases of the patient's normal breathing cycle. This can be achieved by instructing the patient to hold his or her breath at different breathing phases or by using a dynamic CT scan, a commercially available scanning protocol. The dynamic CT scan collects multiple CT images at different phases while a patient breathes normally during scanning.

At process block 74 these multiple CT images are used to develop three dimensional displacement maps at different breathing phases. These displacement maps show displacement of the tissue from a base state (at a given respiration phase, preferably full expiration) and can be obtained by solid modeling or image registration methods.

Referring to FIG. 5 in the solid modeling method, a lung surface 72 is extracted from the CT image of the lung at expiration using image segmentation and surface reconstruction techniques well known in the art. This surface is used to generate a solid finite element model. The solid model is filled with tetrahedral elements 84 with nodes along the middle of each side of the tetrahedron.

The surfaces of lung 76 and 80 at other phases are then extracted to form target surfaces whose shape defines the space that the solid lung model can expand.

The model of the lung surface 72 at full expiration may be loaded with a negative surface pressure so that it expands following the normal physics of a solid material composed of a uniform isotropic substance assuming frictionless contact between the lung and the thoracic wall. It is believed that such a modeling is appropriate for normal quiet breathing.

The lung model expands until the space between the lung model and target surface of the lung at the next phase of respiration is closed. A displacement map between the two phases is then obtained by calculating the corresponding nodal position difference before and after deformation. This process is repeated on the lung surfaces at other breathing phases that CT images are acquired. Displacement maps of any other breathing phases can be interpolated from the results of the two closest phases.

Image set 100 having multiple images at different breathing phases are then created, as indicated by block 78, by using the corresponding displacement map and 3D image warping.

At process block 82, each of the images of the image set 100 so created is linked to a respiration cycle angle R with 100 the image of the image set 100 based on the full expiration lung representing a respiration cycle angle of R=0 degrees and the image of the image set 100 based on the full inspiration lung image 80 representing a respiration cycle angle of R=180 degrees. The images of the image set 100 are preferably a registered respiration cycle angle determined from the corrected respiration signal 50 described above but may alternatively be registered to the lung volume signal 32 alone, the chest displacement signal 44 alone, or a breathing signal based on an internal marker position calculated from the internal marker position in the solid model. A time series of images that simulates patient's breathing is thereby created.

As indicated by process block 88, a dose map 94 (shown in FIG. 13) indicating a desired radiation dose at different positions within the patient with respect to the images for the expiration lung is created using tools and techniques known in the art.

With the knowledge of delivery-respiration phase correspondence, and the dose map 94, beamlet dose distributions (a "treatment plan") are calculated by using the images of the image set 100 at corresponding breathing phase per process block 90.

This treatment plan may then be applied to the patient per process block 92.

Figure 13:
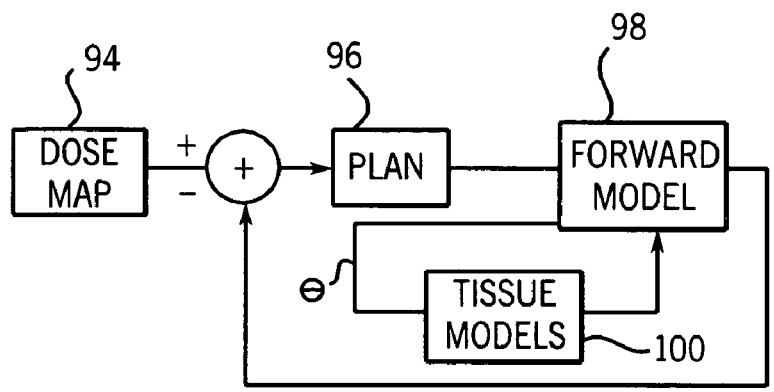
FIG. 13 is a block diagram of the treatment planning system used with intensity modulated radiation therapy and suitable for use with the present invention.

Referring now to FIGS. 1 and 13, these registered images of the image set 100 may be used to generate a treatment plan that accommodates movement of lung and associated tissue per process block 90 through an iterative process. Generally, a treatment plan defines the intensity of multiple rays of the radiation beam 16 for different angles of the radiation source 12 about the patient. The intensities are selected so that the beams at the different angles add with high total intensity on the tumor and add with low intensity on non-tumor tissue.

As described above, a desired tissue dose map 94 is created, for example, as zones superimposed on the image of the expiration lung, each zone mapping desired doses for different elements or node points of the image of the expiration lung. As is understood in the art, the process of determining a treatment plan 96 from a dose map 94 is extremely complex because of the interaction of the multiple rays at different angles. Accordingly, it is common to use an iterative process in which a treatment plan 96 is iteratively adjusted according to one of a number of algorithms, for example, simulated annealing. At each stage of the adjustment, the dose that would result from the treatment plan 96 is modeled per forward model 98. This dose predicted by the forward model 98 is then compared to the desired dose map 94 and the error is used to further adjustment of the treatment plan 96.

The present invention may be integrated into such iterative systems by simply modifying of the forward model 98 to reflect anticipated changes in the lung during the treatment process as captured by the image set 100.

For second generation IMRT, this may be accomplished by assuming that there is a fixed relationship between the angle of the radiation beam 16 and the phase of the breathing cycle. Thus, during modeling in the forward model 98 of the dose, the dose is calculated on a different image of the image set 100 depending on the angle of the radiation beam 16 being considered.

Figures 14, 15:
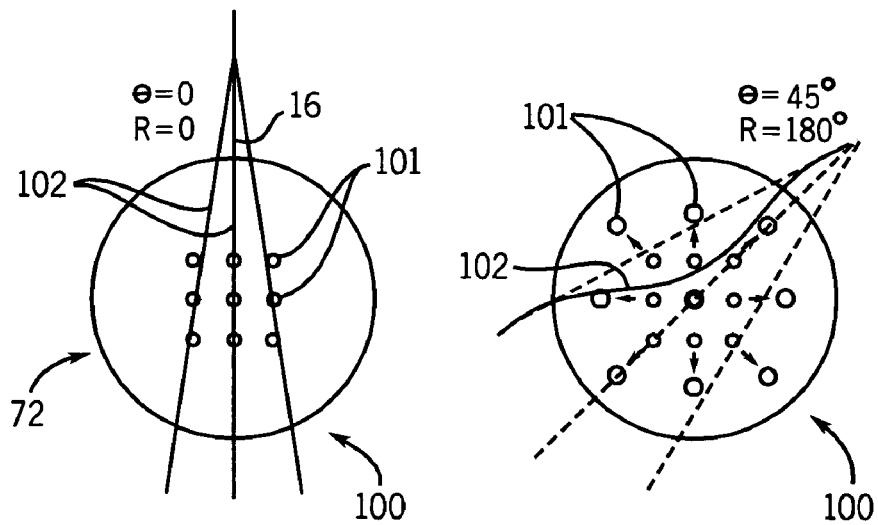
FIGS. 14 and 15 show one method of modification of the dose calculation used in the treatment planning system of FIG. 13 to accommodate lung expansion by modeling curved radiation beams.

Referring now to FIGS. 13, 14, and 15, the forward model 98 may incorporate the expansion of the lung as a function of angle of the beam 16 in a number of ways. In the preferred embodiment, the expansion of the lungs is accommodated by modeling the normally straight beamlets 102 of beam 16 as curved beamlets 102' that follow local tissue dislocations when the lung is expanded.

Thus, as shown in FIG. 14, for a dose map 94 based on the image set of the expiration lung, at a first gantry angle $\theta=0$, and for a respiration cycle angle of R=0, the beamlets 102 of the radiation beam 16 will be modeled in dose map 94 as straight lines through the tissue of image of the expiration lung.

In contrast as shown in FIG. 15, at a later gantry angle $\theta=45$ degrees, at respiration cycle angle of R=180, the lung will conform to the breathing phase associated with full inspiration. In this case, a curved beamlet 102 is used by the dose map 94 based on an expanded image of the image set 100. The curved beamlet 102 allows correct dose placement to be accumulated on the image associated with full expiration by remapping expansion of the tissue to curvature of the beamlet 102. Thus during expansion of the lung, the beamlet 102 curves inward toward the center reflecting the fact that the tissue has in fact expanded relative to the image of the expiration lung used for tallying the total dose.

The treatment plan 96 so generated will differ from a normal treatment plan by describing the intensity of each ray as a function not only of delivery phase but also as a function of respiration cycle angle R. Thus during treatment with the treatment plan 96, the breathing of the patient must be synchronized with the delivery phase $\theta$ and the assumed respiration cycle angle R of the treatment plan 96.

Figure 17:
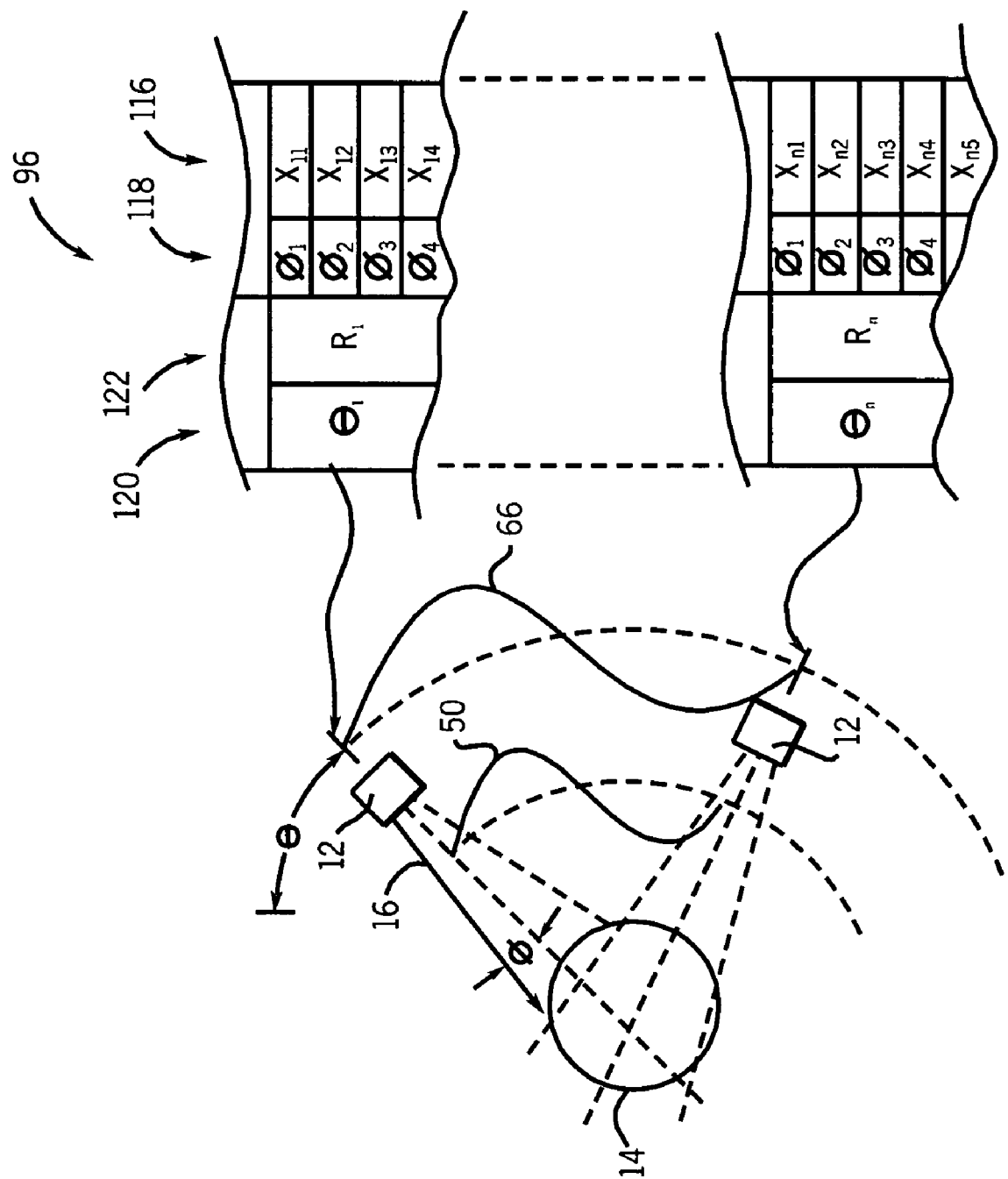
FIG. 17 is a diagram of the motion of the radiation source of the system of claim 1 showing synchronization of the patient's breathing with the standard breathing pattern of the treatment plan.

Referring now to FIG. 17, in a second generation IMRT machine, the radiation source 12 produces a radiation beam 16 comprised of a variety of different rays, each identified from an angle from the center of the beam of $\Phi$. The treatment plan 96 will include intensity values 116 for each of the rays 118 related to given gantry angles 120 and respiratory cycle angles 122. Generally, the mapping of respiration phase 122 to rotational gantry angle 120 will be selected to accommodate the physical constraints of the radiation therapy system 10 in applying radiation and may include a 1:1 mapping in which one 360 degree rotation of the radiation source 12 corresponds to a single breath cycle (360 degrees) or more typically, multiple breath cycles per each rotation of the gantry.

For a first generation IMRT system, the treatment plan 96 must be derived differently because the relationship between delivery phase and breathing phase cannot be as accurately controlled because of mechanical limitations to leaf movement speeds. For this reason, the optimization process must include an additional level of iteration.

In a first step, a set of beamlet intensities is developed using the image at breathing phase R=0 for the several angles of treatment plan anticipated. This treatment plan is prepared using standard planning software for such first generation machines similar to that described with respect to FIG. 13.

The necessary leaf motion sequence to produce the desired beamlet intensities is then calculated by the machine's leaf motion sequence calculator to relate each beamlet intensity to a respiration phase that would exist at the time of the exposure based on movement speed of the shutter and the respiration of the patient following the standard breathing guiding pattern 66. Using these respiration phases, the beamlets are curved, as described above, to reflect the distortion of the tissue caused by respirations. The dose using the beamlet intensities is then recalculated using the curved beamlets. If the dose is within a predetermined tolerance of the desired dose, the planning is complete. Otherwise, the intensities of the beamlets are adjusted using the process of FIG. 13.

At the conclusion of this adjustment, the leaf motion sequence calculator is again used to determine actual respiration phase during the beam exposure and the beamlet curvatures are again adjusted. As before, the dose using the beamlet intensities is then recalculated using the newly curved beamlets. If the dose is within a predetermined tolerance of the desired dose, the planning is complete. Otherwise this process continues to repeat until the desired dose is obtained.

Figure 16:
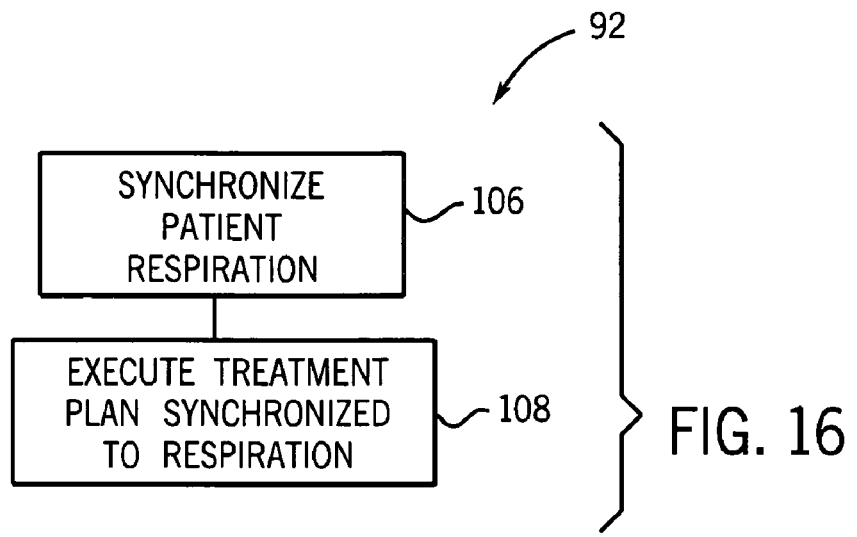
FIG. 16 is a flow chart of the radiation therapy process using the treatment plan generated according to the present invention and breathing control using the corrected respiration signal of the present invention.

Referring now to FIGS. 1 and 16, once the treatment plan 96 has been generated as described, the patient 14 is placed in the radiation therapy machine 10 and the machine prepositioned at a starting angle (e.g., θ=0). The patient 14 then is instructed to match his or her corrected respiration signal 50 with the standard breathing guiding pattern 66 described above with respect to FIG. 9 by watching the display of FIG. 10 as indicated by process block 106.

Once synchronization has been obtained, such as may be determined automatically by the equipment watching the deviation between corrected respiration signal 50 and breathing guiding pattern 66 of FIG. 3, and when the respiration cycle angle R of the breathing guiding pattern 66 matches at the beginning respiration cycle angle R of the treatment plan 96, treatment delivery 96 is initiated. The treatment continues matching its respiration cycle angle (R) 122 to the respiration cycle angle R of the breathing guiding pattern 66 and matching its delivery phase (θ) to the delivery phase θ in plan. In the simplest case, the rate of change of the delivery phase (θ) will be constant and synchronized with the time base of the breathing guiding pattern 66 and the corrected respiration signal 50 will be recorded but does not modify the cycling through of the treatment plan 144. However, it will be understood that a simple modification of this embodiment may allow the delivery phase (θ) to speed up or slow down (together with the gantry in a second generation IMRT machine) to attempt to match changes in the respiration cycle angle R of the patient 14 as indicated by corrected respiration signal 50.

It will be understood that in the present invention, the patient may continue to breathe provided that the patient can control the relative phase of his or her breath. This procedure is much more readily tolerated than breath-hold procedures.

Figure 18:
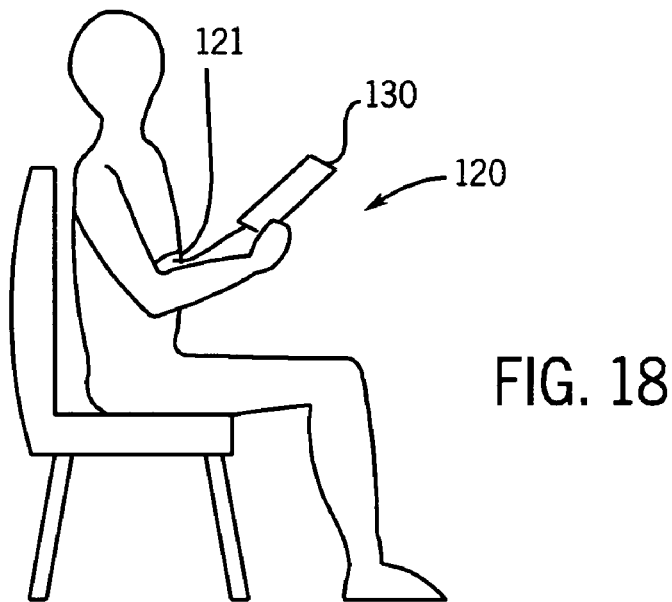
FIG. 18 is a diagram showing a patient using a training system per the present invention.
Figure 19:
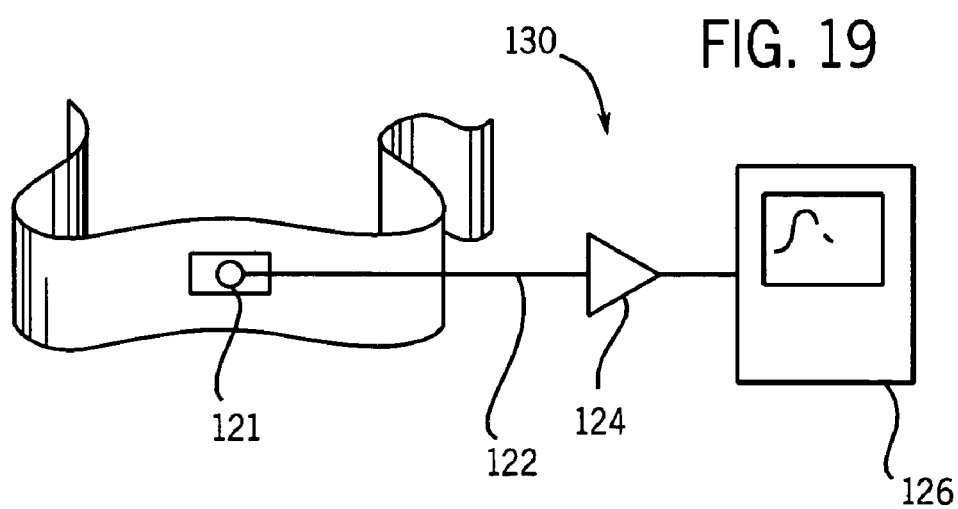
FIG. 19 is a block diagram of the components of the training system of FIG. 18.

In the present invention, the patient may need time to control his or her breathing to track a predetermined breathing schedule during treatment. Referring to FIGS. 18 and 19, a portable patient breathing training system 130 may be used to help patients reduce tracking error. A simple respiratory motion tracking system comprises a pressure sensor 121 detecting abdomen motion. Signals 122 from the pressure sensor 121 are digitized by analog to digital converter 124 and collected on a portable computer such as PDA 126 or the like displaying a stored breathing guiding pattern 66 per FIG. 10 as derived from the patient's normal breathing signal along with a respiration signal derived from the pressure sensor 121.

It is specifically intended that the present invention not be limited to the embodiments and illustrations contained herein, but include modified forms of those embodiments including portions of the embodiments and combinations of elements of different embodiments as come within the scope of the following claims.

We claim:

1. A respiration monitor comprising:
   a spirometer adapted to receive air flow from a patient's lungs with breathing to provide an air flow signal;
   a chest displacement sensor adapted to monitor displacement of the patient's chest with breathing to provide a chest displacement signal;
   a calibration circuit receiving the air flow signal and the chest displacement signal to provide a corrected respiration signal combining information from both the air flow signal and the chest displacement signal;
   an integrator receiving the air flow signal to produce a lung volume signal; and
   a baseline corrector receiving the lung volume signal and the chest displacement signal to correct an integration offset of the lung volume signal to produce the corrected respiration signal based on the chest displacement signal.

2. The respiration monitor of claim 1 wherein the correction of integration offset occurs periodically at a predetermined phase of respiration by setting the lung volume signal equal to a stored calibration value.

3. The respiration monitor of claim 2 wherein the calibration value is a previous value of the lung volume signal at the predetermined phase.

4. A respiration monitor comprising:
   a spirometer adapted to receive air flow from a patient's lungs with breathing to provide an air flow signal;
   a chest displacement sensor adapted to monitor displacement of the patient's chest with breathing to provide a chest displacement signal;
   a calibration circuit receiving the air flow signal and the chest displacement signal to provide a corrected respiration signal combining information from both the air flow signal and the chest displacement signal;
   an integrator receiving the air flow signal to produce a lung volume signal; and
   a model of the relationship between lung volume and chest displacement signal, the model receiving the chest displacement signal to provide a lung volume signal as the corrected respiration signal.

5. The respiration monitor of claim 4 wherein the model is a linear function relating chest displacement signal to lung volume.

6. The respiration monitor of claim 5 wherein the model is a multiplier multiplying the chest displacement signal by a factor determined from a correlation between the lung volume signal and the chest displacement signal to produce the corrected respiration signal.

7. The respiration monitor of claim 4 wherein the model is a non-linear function relating chest displacement signal to lung volume.

8. The respiration monitor of claim 7 wherein the model is a lookup table recording a relationship between lung volume and chest displacement for at least one cycle of breathing, the lookup table receiving chest displacement signal to output the corrected respiration signal.

9. The respiration monitor of claim 4 wherein the model provides a different functional relationship between chest displacement signal and lung volume during inspiration and exhalation.

10. The respiration monitor of claim 4 wherein the model detects a breath-hold from the chest displacement signal and holds the corrected respiration signal constant until an end of the breath-hold.

11. The respiration monitor of claim 1 further including a patient display displaying the corrected respiration signal to the patient.

12. A method of generating a corrected respiration signal comprising the steps of:
   (a) monitoring a patient's breathing with a spirometer adapted to receive air flow from a patient's lungs to provide an air flow signal;

(b) monitoring the patient's breathing with a chest displacement sensor adapted to monitor displacement of the patient's chest with breathing to provide a chest displacement signal;

(c) combining the air flow signal and the chest displacement signal to provide a corrected respiration signal;

(d) integrating the air flow signal to produce a lung volume signal; and (e) using the chest displacement signal to correct an integration offset of the lung volume signal to produce the corrected respiration signal.

13. The method of claim 12 wherein the correction of integration offset occurs periodically at a predetermined phase of respiration by setting the lung volume signal equal to a stored calibration value.

14. The method of claim 13 wherein the stored calibration value is a previous value of the lung volume signal at the predetermined phase.

15. A method of generating a corrected respiration signal comprising the steps of:

(a) monitoring a patient's breathing with a spirometer adapted to receive air flow from a patient's lungs to provide an air flow signal;

(b) monitoring the patient's breathing with a chest displacement sensor adapted to monitor displacement of the patient's chest with breathing to provide a chest displacement signal;

(c) combining the air flow signal and the chest displacement signal to provide a corrected respiration signal;

(d) integrating the air flow signal to produce a lung volume signal; and (e) applying the lung volume signal to a model of the relationship between the lung volume and chest displacement signals to provide a lung volume signal as the corrected respiration signal.

16. The method of claim 15 wherein the model is a linear function relating chest displacement signal to lung volume.

17. The method of claim 16 wherein the model is a multiplier multiplying the chest displacement signal by a factor determined from a correlation between the lung volume signal and the chest displacement signal to produce the corrected respiration signal.

18. The method of claim 15 wherein the model is a non-linear function relating chest displacement signal to lung volume.

19. The method of claim 18 wherein the model is a lookup table recording a relationship between lung volume and chest displacement for at least one cycle of breathing, the lookup table receiving chest displacement signal to output the corrected respiration signal.

20. The method of claim 15 wherein the model provides a different functional relationship between chest displacement signal and lung volume during inspiration and exhalation.

21. The method of claim 15 wherein the model detects a breath-hold from the chest displacement signal and holds the corrected respiration signal constant until an end of the breath-hold.

* * * * *